United States Patent [19]

Itoh et al.

[11] Patent Number: 4,666,581

[45] Date of Patent: May 19, 1987

[54] APPARATUS FOR TWO-DIMENSIONAL ELECTROPHORESIS

[75] Inventors: Michio Itoh, Kokubunji; Isao Ishikawa, Hino; Motoko Yoshida, Chofu; Kazunori Okano, Shiki, all of Japan

[73] Assignee: Hitachi, Ltd., Tokyo, Japan

[21] Appl. No.: 728,234

[22] Filed: Apr. 29, 1985

[30] Foreign Application Priority Data

May 9, 1984 [JP] Japan .................................. 59-90957
Oct. 29, 1984 [JP] Japan ................................ 59-225739

[51] Int. Cl.$^4$ ............................................ G01N 27/26
[52] U.S. Cl. .............................. 204/299 R; 204/182.1; 204/182.8; 204/182.9
[58] Field of Search ............ 204/182.8, 182.9, 299 R, 204/182.7, 182.1, 180 G

[56] References Cited

U.S. PATENT DOCUMENTS 4,297,198 10/1981 Ohashi et al. ................ 204/182.8 X
4,305,799 12/1981 Schwarz et al. .............. 204/182.8 X

FOREIGN PATENT DOCUMENTS 105053 6/1983 Japan .............................. 204/180 G Primary Examiner—John F. Niebling
Assistant Examiner—W. T. Leader
Attorney, Agent, or Firm—Antonelli, Terry & Wands

[57] ABSTRACT

This invention relates to an apparatus for two-dimensional electrophoresis which comprises a supporting plate fixed to a rotary axis, a support for first dimension electrophoresis disposed on the supporting plate and a support for second dimension electrophoresis disposed on another supporting plate. Both the supports are arranged in such a fashion that when the rotary axis is rotated, the support for the first dimension electrophoresis comes on the support for the second dimension electrophoresis or reaches a predetermined position in the support for the second dimension electrophoresis. This arrangement can shift the support for the first dimension electrophoresis to the support for the second dimension electrophoresis without damaging the former.

5 Claims, 6 Drawing Figures

APPARATUS FOR TWO-DIMENSIONAL ELECTROPHORESIS

BACKGROUND OF THE INVENTION

1. Field of the Invention

This invention relates primarily to an apparatus for two-dimensional electrophoresis which simultaneously analyzes multi-components such as those of proteins.

2. Description of the Prior Art

Two-dimensional electrophoresis analysis using a polyacrylamide gel as a support, that has been used conventionally for the multi-component simultaneous analysis of proteins, is conducted in the following manner. (For details, refer to "Proteins.Nucleic Acids-Enzymes", September issue, 1978, page 211, Kyoritsu Shuppan, for example.) First of all, a thinly elongated cylindrical gel containing an ampholyte is prepared inside a glass tube. The gel tube is set up perpendicularly, and an electric field is then applied across both ends of the gel so that the component proteins in the sample added to one of the ends of the gel are separated by the difference of isoelectric points (separated for the first dimension). Next, a slab gel having a concentration gradient of acrylamide is separately prepared between two glass plates (inside a gel holding frame), and the cylindrical gel after the completion of the first dimension separation is extruded from the glass tube and is put on the low concentration end of the slab gel. The gel plate is set up perpendicularly, and a current is caused once again to flow through the slab gel in the direction of its concentration gradient, thereby effecting second dimension separation by the difference of molecular weights. The glass plates interposing the slab gel therebetween are then removed to quantitate the separation proteins. The gel is dipped in a dye solution such as Coomassie blue to stain the proteins and the background is destained. Thereafter, the spots of the stained proteins are quantitated by measuring the absorbance.

However, since the thinly elongated gel used for the first dimension is soft, it is difficult to mechanically carry out the operations of extruding the soft gel from the glass tube and bringing it into close contact with one of the ends of the slab gel without any gap between them. In addition, handling of the soft slab gel after the two-dimensional electrophoresis without breakage of the gel is difficult through a series of operations such as staining, destaining and measurement of absorbence.

SUMMARY OF THE INVENTION

It is an object of the present invention to provide an apparatus for two-dimensional electrophoresis which can easily bring a gel of the first dimension into close contact with a gel of the second dimension without breaking the former.

It is another object of the present invention to provide an apparatus for two-dimensional electrophoresis which comprises a supporting plate fixed to a rotatory axis, a support for first dimension electrophoresis disposed on the supporting plate, and a support for second dimension electrophoresis disposed on another supporting plate, both supports for the first and second electrophoresis being arranged in such a fashion that when the rotary axis is rotated, the support for the first dimension electrophoresis comes on the support for the second dimension electrophoresis or reaches a predetermined position inside the support for the second dimension electrophoresis.

DESCRIPTION OF THE PREFERRED EMBODIMENTS

Figure 1:
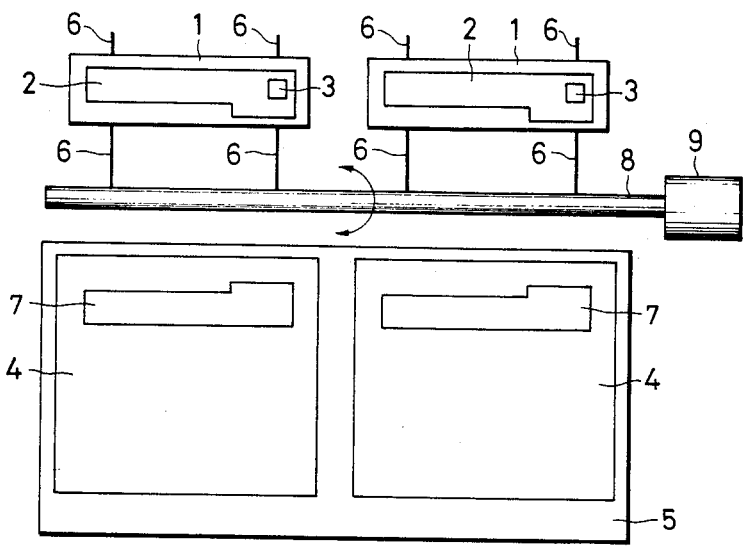
FIGS. 1 and 4 are front views of an apparatus in accordance with one embodiment of the present invention.
Figure 2:
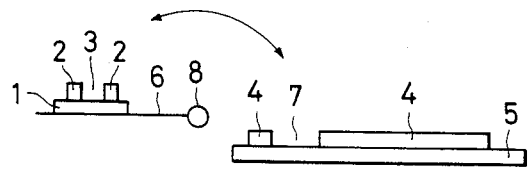
FIGS. 2, 3 and 5 are schematic views useful for explaining the gel movement.

In the apparatus for two-dimensional electrophoresis in accordance with the present invention, one side of each of the supports for the first and second dimension electrophoresis (consisting of acrylamide, agarose or the like) is coupled and fixed to a substrate having mechanical strength (such as glass, polyester or the like), and the first dimension gel can be fitted by rotary motion into the groove that is disposed inside the two dimension gel. If necessary, an agarose solution may be charged into the opening between the first and second dimension gels in order to solidify them and to use them in an integral unitary structure. Since the shift from the first dimension to the second dimension can be made smoothly in accordance with this apparatus, excellent performance and reproducibility can be obtained without deteriorating separation.

Both supports for the first and second dimension are preferably bound to substrates that have been subjected to silane coupling treatment, because the supports can be deposited more strongly on the substrates.

The silane coupling method is carried out in the following manner. After being cleaned and kept clean, the surface of the substrate is activated by alkali treatment (by, for example, dipping the substrate into a 6N NaOH solution, washing it with water and drying). Then, the substrate is subjected to surface treatment using a silane coupling reagent having the following formula:

$$RSiX_3$$

where
R: an organic residue such as a vinyl group, mercaptopropyl group, a methacryloxypropyl group, glycideoxypropyl group, and the like,
X: a compound consisting of an organic residue represented by ethoxy, methoxy, acetoxy, and the like.

In this case, dehydrocondensation develops between the hydroxy group and the X group on the substrate. On the other hand, since bond develops between R and an unsaturated double bond of the gel, acrylamide or the like is fixed to the substrate.

The support for the first dimension is produced in the following manner, for example. A solution consisting of an acrylamide monomer, a cross-linker and a polymerization catalyst is charged into a thinly elongated mold made of an acrylic resin, and a silane coupled glass plate is put on the mold in such a manner as to come into contact with the solution described above. In this case, if a convex is formed on the bottom of the mold, a concave is formed on the gel at the portion where the sample is stored.

The support for the second dimension electrophoresis which has a concentration gradient and whose one surface is fixed is produced in the following manner. 11 cm-square substrates are combined via a spacer in such a manner that the surface which is subjected to silane coupling treatment and the surface which is not treated face one another, and are then charged perpendicularly in the combined state into a container for producing a slab gel. A mixture of an acrylamide monomer, a cross-linker and a polymerization catalyst that has in advance been provided with a continuous concentration gradient in accordance with a predetermined program, thereby forming the concentration gradient, is charged and is then polymerized by the catalytic action of the catalyst to form a polymer gel. A slab gel having a fixed one surface having an arbitrary thickness and an arbitrary concentration can be obtained by changing the spacer and the program. A mold for forming a groove, into which the first dimension gel is buried, is formed at a low acrylamide concentration position at the upper part of the substrate.

Hereinafter, one preferred embodiment of the present invention will be described with reference to FIG. 1.

EXAMPLE 1

After a narrow glass plate represented by reference numeral 1 in FIG. 1 was treated by methacryloxypropyl trimethoxy silane, a thin layer of an acrylamide polymer gel 2 was coupled to the center of the glass plate 1. The polymer gel 2 had a composition consisting of 3.8% acrylamide monomer, 0.2% N,N'-methylene-bis-acrylamide, 0.028% tetramethylethylenediamine, 0.07% ammonium persulfate and 2% ampholite such as "Ampholine", pH 3.5–9.5, produced by LKB Co. The glass plate was fixed on a supporting rod 6 and was placed horizontally. 3 μl of serum was then charged into an opening 3 for sample application on the gel. Both right and left ends of the gel were linked electrically to 0.01M phosphate (anode) and 0.04M sodium hydroxide (cathode), respectively, by filter paper (not shown), and electrophoresis was conducted at 300 V for four hours to separate proteins by the difference of isoelectric points.

On the other hand, a gel 4 having a concentration gradient of 4 to 17%, that was to be used for the second dimension electrophoresis, was similarly coupled to a glass substrate 5 ($110 \times 230 \times 1$ mm) that had been subjected to silane coupling treatment, and a groove 7 for burying the first dimension gel was disposed at the low concentration end of the gel. After the substrate 5 was placed horizontally on a cooling plate, both ends of the gel in the direction of its concentration gradient was bridged to a tris-glycine buffer (pH 8.6) via filter paper (not shown). Immediately after the completion of the electrophoresis, the driving device 9 was operated as represented by arrow in the drawing, so that the glass substrate 1 of the first dimension gel was moved to the groove 7 with the substrate 1 facing up. The gap between the first dimension gel 2 and the groove 7 was filled by low melting temperature agarose. After they were thus integrated, electrophoresis was conducted at 200 V for 3 hours to effect separation by molecular weights. After the completion of the two dimension electrophoresis, the gel 4 was stained together with the substrate 5 by Coomassie blue R250 dye solution (containing 50% methanol and 7% acetic acid), and destaining of the background was effected in a 7% aqueous acetic acid solution. The procedures described above could provide the separated spot images of about 100 kinds of proteins.

Although the embodiment described above describes an apparatus for simultaneously producing two electrophoretic images, a large number of electrophoretic separation images can be produced simultaneously and reproducibly by fixing naturally a large number of first dimension gels to the rotary axis 8.

In FIG. 1, the supporting rod 6 and the rotary axis 8 are preferably made of an insulator in order to prevent the short-circuit of the electrophoretic current.

Figure 3:
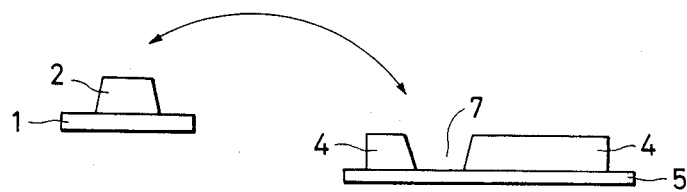

Fitting of the two gels can be made accurately and a better result can be obtained by using a gel 2 having a trapezoidal cross-section as shown in FIG. 3, the gel for the first dimension electrophoresis, and a groove 7 having an inverted trapezoidal cross-section, the groove on the gel for the second dimension to accep the gel 2.

Figure 4:
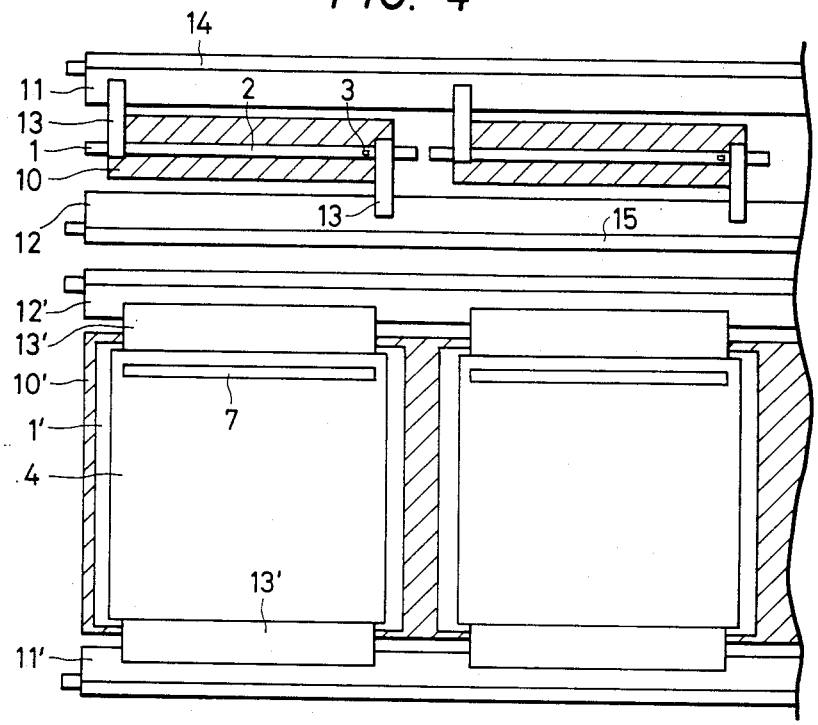

Referring again to FIG. 1, the substrate 1 is shown wider than the gel 2, but their width may be equal. Such an example is illustrated in FIG. 4.

A gel 2 for the first dimension electrophoresis (for example, an acrylamide gel for the separation by isoelectric points) whose one surface was coupled and fixed and whose other surface was open was placed on a substrate 1, and each substrate 1 was aligned on a cooling plate 10. The cooling plate 10 had a construction in which a Peltier device was brought into close contact with the lower surface of a highly insulated and highly heat conductive plate (for example, SiC plate), and a thermal sensor assembled in the highly heat conductive plate passed a current through the Peltier device to cool the same. (The wiring to the Peltier device is not shown in the drawing.) Electrolyte bridge materials 13 (such as filter paper) were arranged at right angles to the supports so that both ends of the gel for the first dimension electrophoresis could keep the electrolyte bridge with the anolyte and catholyte in electrolyte containers 11 and 12 that were disposed in parallel with each other so as to interpose each cooling plate 10 between them. Electrodes 14, 15 were disposed inside electrolyte containers 11, 12, so that a voltage could be applied to each terminal. Reference numeral 3 represents a hole for sample application.

After the completion of the first dimension electrophoresis, the exposed portions of the substrate extending from both ends of the gel were clamped by supporting members (not shown), and were buried in the grooves 7 of the adjacent gels for the second dimension electrophoresis (for example, on the low concentration side of the polyacrylamide concentration gradient gel). The cooling plate 10' was also disposed below the substrate 1' under the gel 4 for the second dimension electrophoresis.

Two or more sets of the gel for the first dimension electrophoresis and the gel for the second dimension electrophoresis were disposed transversely in the drawing, and up to 30 sets could be simultaneously moved by the later-appearing gel moving device. However, a preferred system can move five to twenty sets at the same time.

Figure 5:
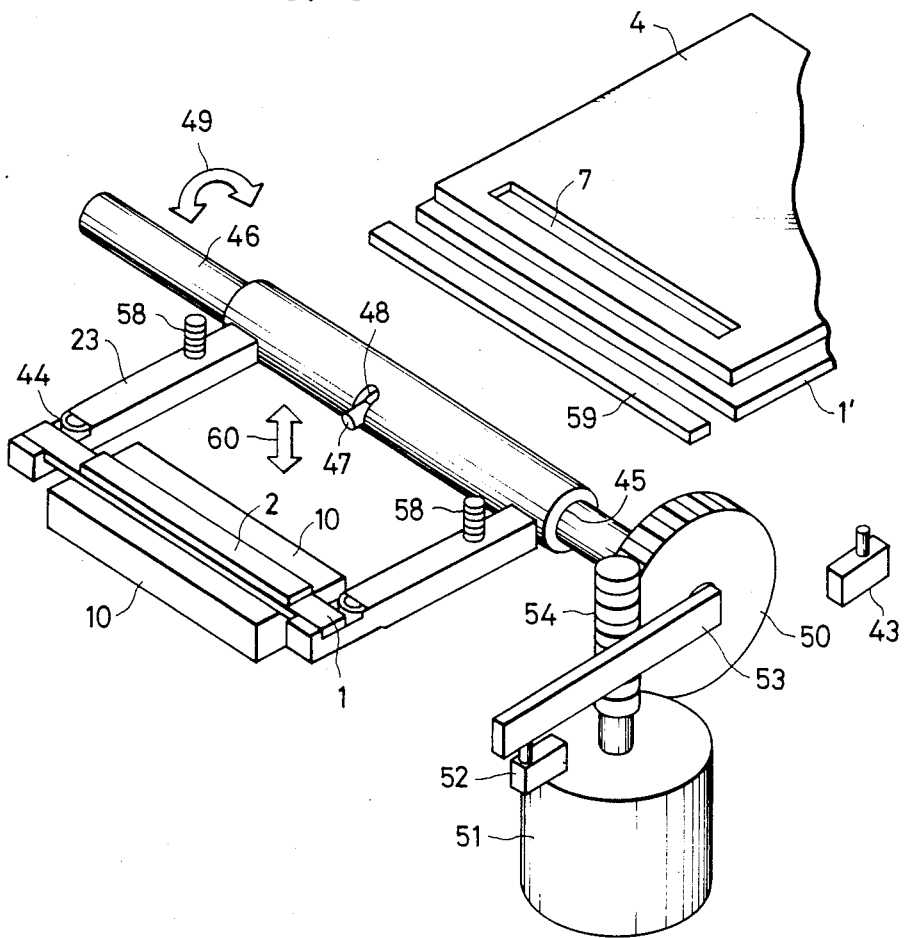

FIG. 5 shows an example of the gel moving mechanism in accordance with the present invention. In the drawing, the forward and rear portions of the substrate 1, on which the gel 2 for the first dimension electrophoresis is placed, are clamped by springs 44 so that the substrate 1 is fixed on a rotary arm 23. A shaft 46 is fitted into a rotary hole 45 of the arm 23, and the shaft 46 and the arm 23 are coupled by a pin 47. A groove 48 of the arm 23 into which the pin 47 for fitting the arm to the shaft 46 is elongated in the rotating direction represented by arm 49, and the shaft 46 and the arm 23 are coupled with a chink in the rotating direction. A worm wheel 50 is fitted to the other end of the shaft 46, and another worm wheel 54 is fixed to the shaft of a motor 51. A dog 53 is fitted to this worm wheel 54 in order to control the motor 51 during the rotation of the worm wheel. Since limit switches 52 and 43 come into contact with the dog 53, the motor 51 is controlled. In other words, the electrophoresis of the gel for the first dimension electrophoresis is effected at the position of the limit switch 43, and the second dimension electrophoresis is effected at the position of the limit switch 52 when the rotary shaft 46 rotates subsequently.

The gel 4 for the second dimension electrophoresis is disposed on the opposite side to the gel 2 for the first dimension electrophoresis. After the gel 2 for the first electrophoresis comes into contact and overlap with the position of the groove 7 of the gel 4 for the second dimension electrophoresis, a voltage is applied across both ends of the gel 4 to conduct electrophoresis. A spring 58 is fitted into the arm 23 in order to locate the gel 2 for the first dimension in the rotating direction. This spring 58 strikes a fixed plate 59 when the arm 23 rotates toward the gel 4 for the second dimension electrophoresis, and reduces the contact pressure of the gel 2 for the first dimension electrophoresis to the gel 4 for the second dimension electrophoresis. If this contact pressure is excessively great, the gel will be broken and the electrophoresis can not be effected any longer. The position of the limit switch 43 for controlling the motor 51 is adjusted so that the motor 51 stops within the range of the chink in the direction of the arrow 49 of the arm 23.

Though the above explains only one electrophoretic apparatus, the shaft 46 is elongated in the axial direction in practice, and a plurality of arms 23 are disposed so that a plurality of gels for electrophoresis can be moved simultaneously.

Figure 6:
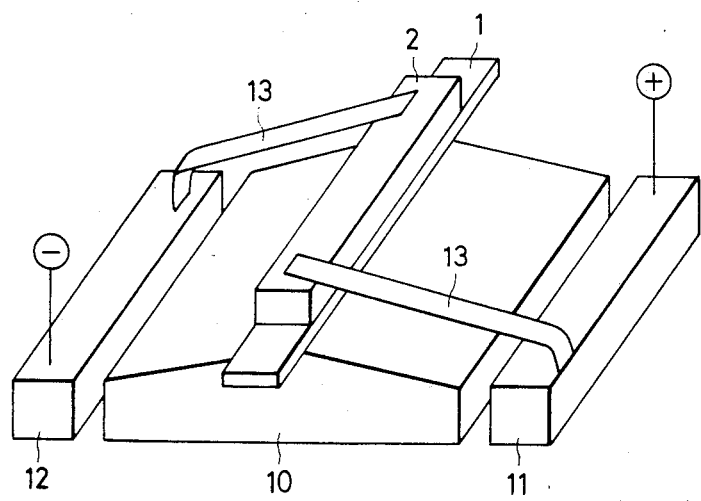
FIG. 6 is a partial perspective view of another embodiment of the present invention.

FIG. 6 illustrates another embodiment of the present invention, in which only one of the portions for the first dimension electrophoresis is shown. If the cooling plate is greater than the substrate and any deflection occurs on the electrolyte bridge material, the electrolyte bridge material comes into contact with the cooling plate, so that the electrolyte spreads over the cooling plate and will cause the leakage of the current. Therefore, a uniform current does not flow through the gel, and the reproducibility of electrophoresis will be reduced.

To cope with the problem described above, both ends of the cooling plate 10 are inclined as shown in FIG. 6, and the electrolyte bridge material 13 are likewise inclined towards the electrolyte containers 11 and 12. The inclination of the cooling material 10 is preferably from about 10 to about 35 degrees so that even when the electrolyte spills, it can drain well. If the inclination is below 5 degrees, deflection will occur, and if the inclination is above 30 degrees, the contact between the gel and the electrolyte bridge material will become unstable.

As described above, the apparatus of the present invention can eliminate the necessity of directly handling the gel-like electrophoretic supports for the first and second dimension electrophoresis, but can handle the gels with their substrates and can simplify the procedures. Particularly because the shift from the gel for the first dimension electrophoresis to the gel for the second dimension electrophoresis can be made by the simplest rotary motion without any manual works, a large number of samples can be analyzed with high reproducibility.

What is claimed is:

1. An apparatus for two-dimensional electrophoresis comprising a supporting plate fixed to a rotary axis, a support for the first dimension electrophoresis disposed on said supporting plate and a support for the second dimension electrophoresis disposed on another supporting plate, both of said supports being so arranged that when said rotary axis is rotated, said support for the first dimension electrophoresis reaches a predetermined position on or in said support for the second dimension electrophoresis; a section of said support for the first dimensional electrophoresis being trapezoidal, and said support for the second dimension electrophoresis having a groove the sides of which define an inverted trapezoidal section which corresponds to the trapezoidal section of said support for the first dimension electrophoresis.

2. An apparatus for two-dimensional electrophoresis comprising a supporting plate fixed to a rotary axis, a support for the first dimension electrophoresis disposed on said supporting plate and a support for the second dimension electrophoresis disposed on another supporting plate, both of said supports being so arranged that when said rotary axis is rotated, said support for the first dimension electrophoresis reaches a predetermined position on or in said support for the second dimension electrophoresis; a plurality of sets each consisting of said support for the first dimension electrophoresis and said support for the second dimension electrophoresis being provided, said supports being gels, and each of the gels for the first dimension electrophoresis being electrolytically bridged at both of its ends to anolyte and catholyte containers for the first dimension electrophoresis by an electrolyte bridge material disposed substantially at right angles to the electrophoretic direction.

3. An apparatus for two-dimensional electrophoresis comprising a supporting plate fixed to a rotary axis, a first gel support for a first dimension electrophoresis disposed on said supporting plate and a second gel support for a second dimension electrophoresis disposed on another supporting plate, said second gel support having an opening therein, both of said gel supports being so arranged on said support plates that when said rotary axis is rotated, said first gel support for the first dimension electrophoresis reaches a predetermined position within the opening of said the second gel support for second dimension electrophoresis.

4. The apparatus for two-dimensional electrophoresis as defined in claim 3, wherein said first gel support for the first dimension electrophoresis has a trapezoidal cross-section and the opening in said second gel support for the second dimension electrophoresis defines an inverted trapezoidal shaped groove into which said first gel support is located at said predetermined position.

5. The apparatus for two-dimensional electrophoresis as defined in claim 3, wherein a plurality of sets each consisting of said first gel support for the first dimensional electrophoresis and said second gel support for the second dimension electrophoresis are provided, and each of the first gel supports for the first dimension electrophoresis being electrolytically bridged at both ends to anolyte and catholyte containers, respectively, for the first dimension electrophoresis by an electrolyte bridge material disposed substantially at right angles to the electrophoresis direction.

* * * * *